United States Patent
Westlund et al.

(10) Patent No.: US 6,671,560 B2
(45) Date of Patent: Dec. 30, 2003

(54) MODIFIED GUIDEWIRE FOR LEFT VENTRICULAR ACCESS LEAD

(75) Inventors: Randy W. Westlund, Minneapolis, MN (US); Bruce A. Tockman, Scandia, MN (US); Randall M. Peterfeso, St. Paul, MN (US); John S. Greenland, San Diego, CA (US); Mary N. Hinders, Murrieta, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 10/081,436

(22) Filed: Feb. 20, 2002

(65) Prior Publication Data

US 2002/0077686 A1 Jun. 20, 2002

Related U.S. Application Data

(63) Continuation of application No. 09/466,266, filed on Dec. 17, 1999, now Pat. No. 6,356,791, which is a continuation-in-part of application No. 09/164,891, filed on Oct. 1, 1998, now abandoned, which is a continuation-in-part of application No. 09/097,101, filed on Jun. 12, 1998, now abandoned.

(51) Int. Cl.[7] ............................................. A61N 1/05
(52) U.S. Cl. ........................ 607/116; 607/119; 607/122
(58) Field of Search ............................... 607/115, 116, 607/119, 122, 125

(56) References Cited

U.S. PATENT DOCUMENTS 3,769,984 A  11/1973  Muench ....................... 607/122

(List continued on next page.)

FOREIGN PATENT DOCUMENTS

| CA | 2178934 | 4/1996 | .......... A61M/25/01 |
|---|---|---|---|
| DE | 195 09 609 | 10/1995 | .......... A61F/2/48 |
| EP | 0 057 877 B1 | 8/1982 | .......... A61N/1/04 |
| EP | 0 057 877 A1 | 8/1982 | .......... A61N/1/04 |
| EP | 0 388 480 A1 | 9/1990 | .......... A61N/1/05 |
| EP | 0 709 111 A2 | 5/1996 | .......... A61N/1/05 |
| EP | 0 709 111 A3 | 11/1997 | .......... A61N/1/05 |
| GB | 2 032 278 A | 5/1990 | .......... A61M/25/00 |
| WO | 388480 | 9/1990 | .......... A61N/1/05 |

OTHER PUBLICATIONS

Advances in Pacemaker Technology (M. Schaldach et al. eds., Springer–Verlag, 1975) pp. 30–31.

Research Disclosure, "Guidewire Placement of Electrical Lead," Oct. 1993, p. 685.

*Primary Examiner*—Carl Layno
(74) *Attorney, Agent, or Firm*—Finnegan, Henderson, Farabow, Garrett & Dunner, LLP (57) ABSTRACT

An improved guidewire for assisting in implantation of a cardiac lead includes three sections. The most distal zone is sufficiently floppy to prevent trauma to the vessel walls through which the guidewire and lead are inserted. An intermediate zone is generally stiffer and has a cross-section less than or equal to the cross-section of the distal zone. The third zone is stiffer yet and is joined to the intermediate zone by a shoulder. The shoulder cooperates with protrusions on the lead to transfer forces between the guidewire and lead. A removal wire having temporary locking device to lock the removal wire to the lead is employed to remove the guide catheter without moving the lead from its desired location. Lubricious coatings are also provided to reduce friction between the lead and guidewire.

49 Claims, 4 Drawing Sheets

U.S. PATENT DOCUMENTS

| | | | |
|---|---|---|---|
| 4,011,875 A | 3/1977 | Lehr et al. .................... | 607/128 |
| 4,106,512 A | 8/1978 | Bisping ....................... | 607/127 |
| 4,146,036 A | 3/1979 | Dutcher et al. .............. | 607/127 |
| 4,185,639 A | 1/1980 | Linder ................... | 128/200.26 |
| 4,217,913 A | 8/1980 | Dutcher ...................... | 607/127 |
| 4,282,885 A | 8/1981 | Bisping ....................... | 607/127 |
| 4,311,153 A | 1/1982 | Smits ......................... | 607/127 |
| 4,355,646 A | 10/1982 | Kallok et al. ............... | 607/122 |
| 4,667,686 A | 5/1987 | Peers-Travarton .......... | 607/127 |
| 4,932,407 A | 6/1990 | Williams ....................... | 607/5 |
| 4,934,381 A | 6/1990 | MacGregor ................. | 607/116 |
| 4,943,289 A | 7/1990 | Goode et al. ............... | 606/108 |
| 5,003,990 A | 4/1991 | Osypka ....................... | 600/585 |
| 5,011,482 A | 4/1991 | Goode et al. ............... | 606/108 |
| 5,013,310 A | 5/1991 | Goode et al. ............... | 606/108 |
| 5,014,696 A | 5/1991 | Mehra ........................... | 607/5 |
| 5,016,646 A | 5/1991 | Gotthardt et al. ........... | 607/122 |
| 5,099,838 A | 3/1992 | Bardy ............................ | 607/2 |
| 5,103,837 A | 4/1992 | Weidlich et al. ............ | 607/120 |
| 5,207,683 A | 5/1993 | Goode et al. ............... | 606/108 |
| 5,234,437 A | 8/1993 | Sepetka ....................... | 606/108 |
| 5,243,996 A | 9/1993 | Hall ............................ | 600/585 |
| 5,299,580 A | 4/1994 | Atkinson et al. ........... | 600/585 |
| 5,304,218 A | 4/1994 | Alferness .................... | 607/122 |
| 5,313,943 A | 5/1994 | Houser et al. .............. | 600/374 |
| 5,324,324 A | 6/1994 | Vachon et al. .............. | 607/120 |
| 5,348,021 A | 9/1994 | Adams et al. .............. | 600/521 |
| 5,350,404 A | 9/1994 | Adams et al. ................ | 607/5 |
| 5,381,790 A | 1/1995 | Kanesaka .................... | 600/381 |
| 5,433,729 A | 7/1995 | Adams et al. ................. | 607/5 |
| 5,458,621 A | 10/1995 | White et al. ................... | 607/5 |
| 5,476,498 A | 12/1995 | Ayers ......................... | 607/122 |
| 5,487,385 A | 1/1996 | Avitall ........................ | 600/374 |
| 5,507,301 A | 4/1996 | Wasicek et al. ............. | 600/585 |
| 5,509,411 A | 4/1996 | Littmann et al. ........... | 600/381 |
| 5,514,173 A | 5/1996 | Rebell et al. ............... | 607/127 |
| 5,520,194 A | 5/1996 | Miyata et al. .............. | 600/585 |
| 5,545,204 A | 8/1996 | Cammilli et al. ........... | 607/123 |
| 5,562,275 A | 10/1996 | Weissenfluh et al. ....... | 267/155 |
| 5,584,873 A | 12/1996 | Shoberg et al. ............. | 607/122 |
| 5,609,622 A | 3/1997 | Soukup et al. .............. | 607/122 |
| 5,643,231 A | 7/1997 | Lurie et al. .................. | 604/532 |
| 5,755,765 A | 5/1998 | Hyde et al. ................. | 607/122 |
| 5,782,239 A | 7/1998 | Webster, Jr. ................ | 600/374 |
| 5,782,760 A | 7/1998 | Schaer ....................... | 600/381 |
| 5,803,928 A * | 9/1998 | Tockman et al. ........... | 607/122 |
| 5,897,819 A | 4/1999 | Miyata et al. .............. | 264/103 |
| 5,910,364 A | 6/1999 | Miyata et al. .............. | 428/375 |
| 5,935,160 A * | 8/1999 | Auricchio et al. .......... | 607/122 |
| 5,957,842 A | 9/1999 | Littmann et al. ........... | 600/381 |
| 6,141,576 A | 10/2000 | Littmann et al. ........... | 600/381 |
| 6,192,280 B1 | 2/2001 | Sommer et al. ............. | 607/122 |
| 6,240,321 B1 | 5/2001 | Janke et al. ................. | 607/122 |
| 6,356,791 B1 * | 3/2002 | Westlund et al. ........... | 607/115 |
| 6,377,856 B1 * | 4/2002 | Carson ....................... | 607/122 |
| 6,408,213 B1 * | 6/2002 | Bartig et al. ................ | 607/122 |

* cited by examiner

MODIFIED GUIDEWIRE FOR LEFT VENTRICULAR ACCESS LEAD

CROSS REFERENCE TO THE RELATED APPLICATION

This patent application is a continuation of application Ser. No. 09/466,266, filed Dec. 17, 1999, which is a continuation-in-part of application Ser. No. 09/164,891 filed Oct. 1, 1998 now abandonded, which was a continuation-in-part of application Ser. No. 09/097,101, filed Jun. 12, 1998, now abandoned.

BACKGROUND OF THE INVENTION

I. Field of the Invention

The invention relates to the implantation and placement of cardiac leads used in combination with cardiac rhythm management devices, e.g., heart pacemakers or defibrillators, to monitor and control the rhythm of the heart. This invention is more particularly directed toward a guidewire/pacing lead configuration adapted to assist in the implantation and placement of a cardiac lead having one or more electrodes that are to reside in the distal branches of the coronary venous system, the great cardiac vein, or coronary sinus. The invention also encompasses the use of a guide catheter along with a guidewire and removal wire configurations useful in removing guide catheters without dislodging the implanted leads.

II. Discussion of the Prior Art

Placement of cardiac leads in the distal branches of the coronary venous system, the great cardiac vein, or the coronary sinus is a difficult task. Often when deploying the lead there comes a point at which the lead cannot be advanced further into the vascular system using standard techniques and equipment. All too often this point is not the optimal position for the lead's electrode, either for sensing cardiac electrical activity or delivering pacing therapy to the heart.

There are several reasons which make proper placement of the lead difficult. These include (1) friction between the vasculature and the lead; (2) partial obstruction of the vasculature; (3) unusually shaped bifurcations in the vasculature; and (4) accumulative friction between lead, guide catheter and guidewire. Prior efforts to resolve such problems included the use of a stiffer guidewire. While stiffer guidewires offer additional support, they may impede advancement due to their relative size with respect to the lumen of the lead. Additionally, when proper placement of the lead is achieved, problems arise during guide catheter or guidewire extraction. All too often, the act of extracting the guide catheter and/or guidewire causes the lead to be dislodged from the implanted position. Standard guidewires and stylets are not suitable for maintaining position while the guide catheter is removed due to insufficient stiffness, lack of appropriate force transmission features, and friction between the guidewire and lumen wall of the coronary vein lead. A means must be provided which will hold the lead and its corresponding electrodes in place while allowing the guide catheter and guidewire to be removed.

The present invention is deemed to be an improvement over conventional prior art guidewires. It is more effective in properly placing the lead and it is also less likely to cause a properly placed lead to become dislodged during extraction of the guide catheter and the guidewire itself.

SUMMARY Of THE INVENTION

In cases where the over-the-wire lead is to be implanted without the aid of a guide catheter, the guidewire may be of a uniform stiffness along its length except at a distal end portion where there is attached a floppy segment comprising a coiled wire helix having a very thin, flexible core member extending through the center of the helix and with the distal end of the core wire affixed to an atraumatic tip. The stiffness of the guidewire is designed to be less than the stiffness of the lead with which it is used. The lead is of the type having an elongated, flexible, polymeric lead body with a lumen extending the full length thereof from a proximal end to a distal end and of a cross-section allowing the guidewire to extend therethrough as the lead body is advanced over the guidewire in placing the lead's electrode(s) at a desired location within the patient's vasculature.

Because the lead has a somewhat greater stiffness property than its associated guidewire, there are greater frictional forces between the lead and the vessel in which it is placed than between the guidewire and the wall of the lead body defining the lead's lumen. Hence, the guidewire can be removed from the lead without dragging the lead with it.

In instances where a guide catheter is first advanced through a blood vessel and into the ostium of the coronary sinus before the guidewire is inserted and the lead advanced over the guidewire, it may become necessary to utilize a removal wire to hold the lead against movement as the surrounding guide catheter is removed subsequent to removal of the guidewire. The removal wire includes an element for engaging the lead and holding it stationary as the guide catheter is stripped free of the pacing lead body.

In accordance with a second embodiment of the present invention, there is provided a guidewire comprised of at least three zones. Each zone differs from the other two in terms of its stiffness and flexibility. Each zone also has geometric characteristics which assist in proper placement of the lead and further assist in preventing dislodgement of the lead as the guide catheter is extracted and as the guidewire itself is extracted.

Specifically, the first and most distal zone is intended to be very floppy to prevent trauma to the surrounding vessel walls when the guidewire is being advanced beyond the distal end of a guide catheter when deploying a coronary vein lead. This distal zone may include a spiral wound portion surrounding a thin, solid ribbon core and a spherical tip. The second zone is relatively more stiff than its adjacent distal section and may comprise a solid wire or spiral wound wire having a cross-sectional diameter that does not exceed the cross-sectional diameter of the first zone. The second and most proximal zone is preferably of a larger diameter and is somewhat stiffer than the first zone but not as stiff and flexible as the lead body in which it is inserted. The second zone comprises a wire or hypo tube which can be manipulated to apply advancement forces during deployment of the lead and stabilizing forces to a lead during extraction of the guide catheter. A diametric transition between the first and second zones is abrupt and ideally corresponds to a matching feature in the lead so that this transition is the point where most of the advancement forces and counter forces are transmitted to the lead.

In a third embodiment, a removal wire is provided which has a squared end for engaging a portion of the lead to hold it in place during guide catheter removal. The guide catheter easily disengages from the lead for withdrawal of the removal wire.

In yet another embodiment a three zone removal wire is used which extends beyond the length of the guide catheter, but does not exit the lead to frictionally hold the lead in place while removing the guide catheter.

In still another embodiment the three zone removal wire is provided with a temporary locking means to hold the lead in place while removing the guide catheter. The temporary locking means can be proximal, distal or both. The temporary locking means can also be along the length of the removal wire or in the lumen of the lead.

In a further embodiment the removal wire with the temporary locking means can be modified to have only one zone.

Other improvements also exist. For example, the improved guidewire (or portions thereof) can be provided with a hydrophilic coating to produce a highly lubricious surface. The presence of such a surface reduces friction between the lumen wall of the lead and the guidewire thereby reducing the risk that the lead will be dislodged during extraction of the guidewire.

DESCRIPTION OF THE DRAWINGS

The foregoing features, objects and advantages of the present invention will become more clear to those skilled in the art from the following detailed description of a preferred embodiment, particularly when considered in conjunction with the accompanying drawings in which like numerals in the several views refer to corresponding parts.

DETAILED DESCRIPTION OF THE INVENTION

Figures 1, 1A, 1B:
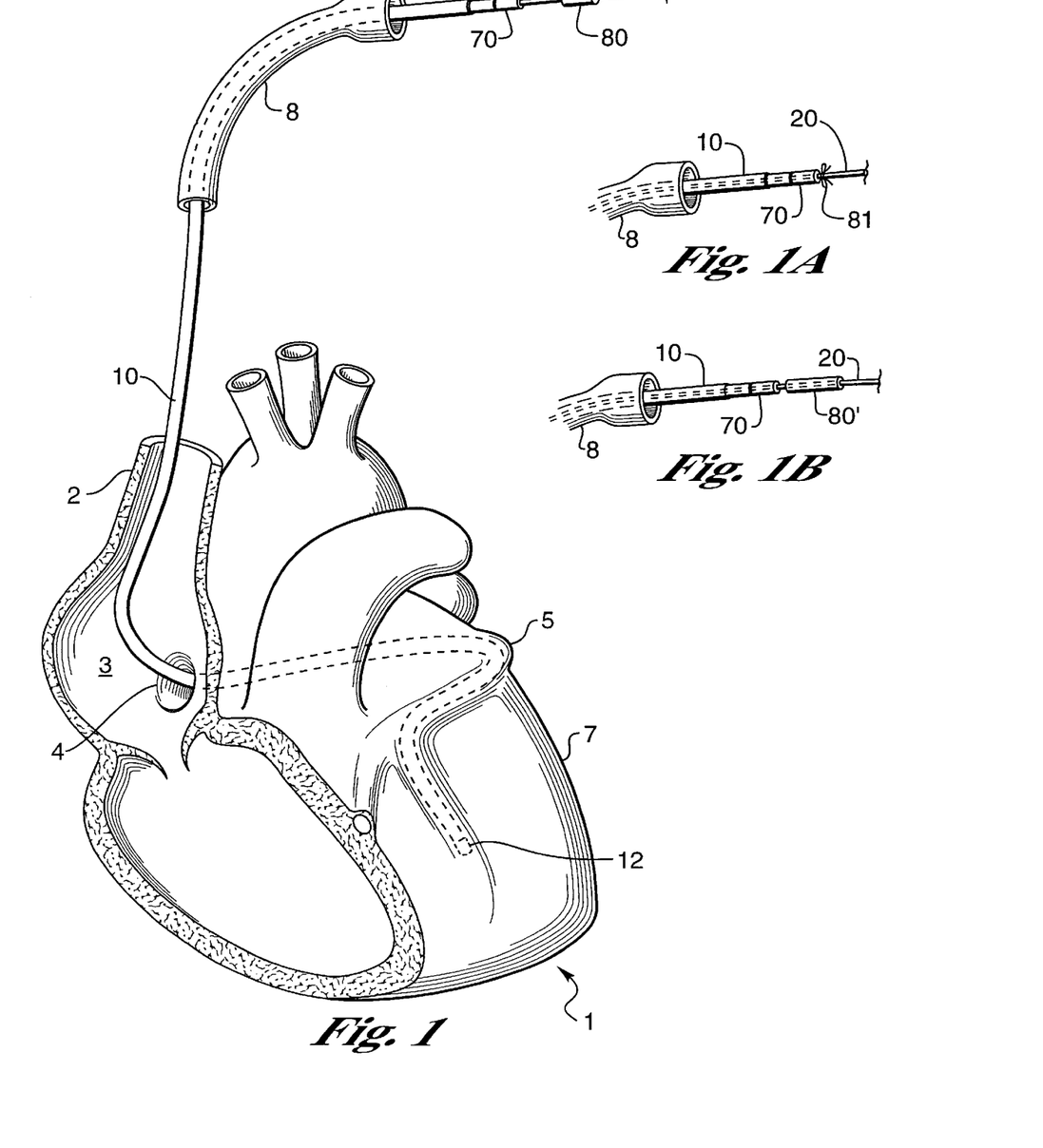
FIG. 1 is a view showing an intravenous cardiac lead having an electrode positioned in a coronary vein, a segment of a guide catheter, a removal wire and a proximal end locking means.
FIG. 1A is a fragmentary view showing an alternative locking mechanism.
FIG. 1B is a fragmentary view showing a further alternative locking mechanism.

FIG. 1 shows a human heart 1 with a coronary lead 10 passing through the superior vena cava 2, the right atrium 3, and the coronary sinus 4 into the great vein 5 of the heart 1 so that an electrode 12 on the lead 10 is properly positioned in a branch of the coronary vein on the left sides of the heart. When positioned as shown, the electrode 12 can be used to either sense the electrical activity of the heart or to apply stimulating pulses to the left ventricle 7 without the electrode being positioned within the left ventricular chamber. A portion of a guide catheter 8 is used to insert the lead into the heart 1. The present invention is concerned with guidewires and/or removal wires useful for placing leads 10 and their electrodes in the vasculature and for removing the associated guide catheter 8 and a guidewire 20 without dislodging the leads 10 and its electrode(s) 12. As used herein, the term "guidewires" includes both the guidewires used to install the leads and "removal wires" also known as "removal wires" used for removing the guide catheter without moving the leads. In some embodiments disclosed herein the guidewires also function as removal wires and in others, a separate guidewire and removal wire is employed.

Figure 2:
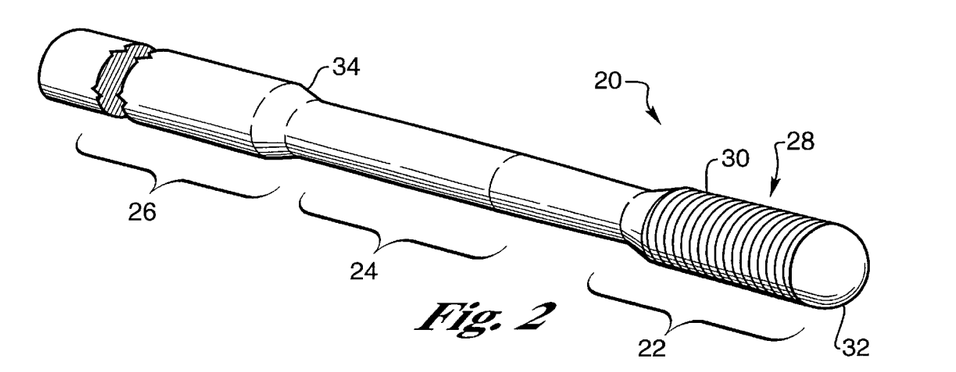
FIG. 2 is a perspective view of a preferred embodiment of a guidewire of the present invention.

FIG. 2 shows a first preferred embodiment of a guidewire 20 advantageously used to position the coronary lead 10 as shown in FIG. 1 and retain the coronary lead in that position as the guide catheter 8 is removed. Guidewire 20 in FIG. 2 has three zones, a distal zone 22, intermediate zone 24, and a proximal zone 26. As will be later described, a two zone guidewire can also be employed in the practice of the invention.

Figure 6:
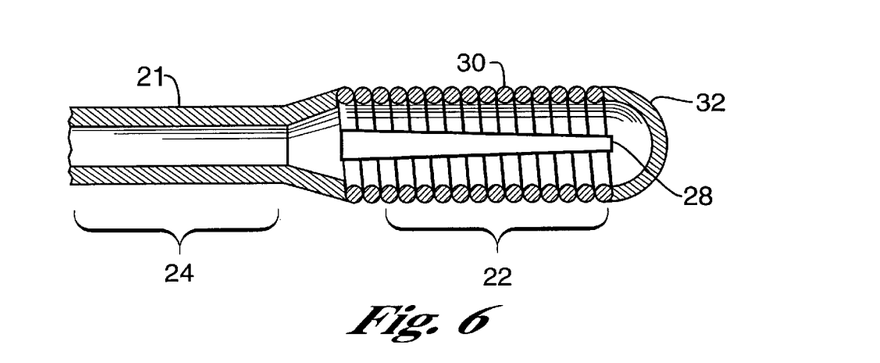
FIG. 6 is a cross-section of the distal zone of the guidewire shown in FIG. 1.

With continued reference to FIG. 2, the distal zone 22, as best seen in FIG. 6, preferably may be about 1 to 1.5 inches long. The distal zone 22 is circular in cross-section and may have a cross-sectional diameter of approximately 0.014 inches. The distal zone 22 comprises an internal shapeable ribbon core member 28 (FIG. 6), a spiral winding 30 and a spherical tip 32. The internal ribbon core member 28, as it extends distally, may taper from about 0.005 inches to about 0.001 inches. This construction is sufficiently floppy such that there is no trauma induced by the guidewire to a surrounding vessel wall as the guidewire is advanced through the vasculature. This construction also allows it to be capable of being biased so as to aid in steering through the vasculature.

The intermediate zone 24 is generally slightly stiffer than the distal zone 22. The intermediate zone may comprise a solid wire having a circular cross-section. The cross-sectional diameter of the wire can vary depending upon the performance needs, but should not exceed the cross-sectional diameter of distal zone 22. The length of intermediate zone 24 can also vary, but preferably will be one to four inches long.

The proximal zone 26 is made of a wire or tubing and is the stiffest and longest section of the guidewire 20. The proximal zone 26, being the stiffest and most proximal, is the portion handled and used by the medical professional to apply forces during deployment and guide catheter extraction. Preferably, the overall length of the guidewire 20 will be in the range of four to five feet. The cross-sectional diameter of the proximal zone 26 is larger than the cross-sectional diameter of the distal zone 22 and the intermediate zone 24. For example, if the distal and intermediate zones have a diameter of approximately 0.014 inches, the proximal zone could have a diameter of approximately 0.022 inches. The diametrical transition between the proximal and intermediate zones taper, though abruptly, from about 0.022 inches to about 0.014 inches. As discussed below, this diametrical transition constitutes a shoulder 34 through which most of the advancement and stabilizing forces are transmitted between the lead 10 and guidewire 20 during insertion of the guidewire 10 and extraction of the guide catheter 8. The dimensions set out herein are intended to be illustrative, but not limitive.

Figure 3:
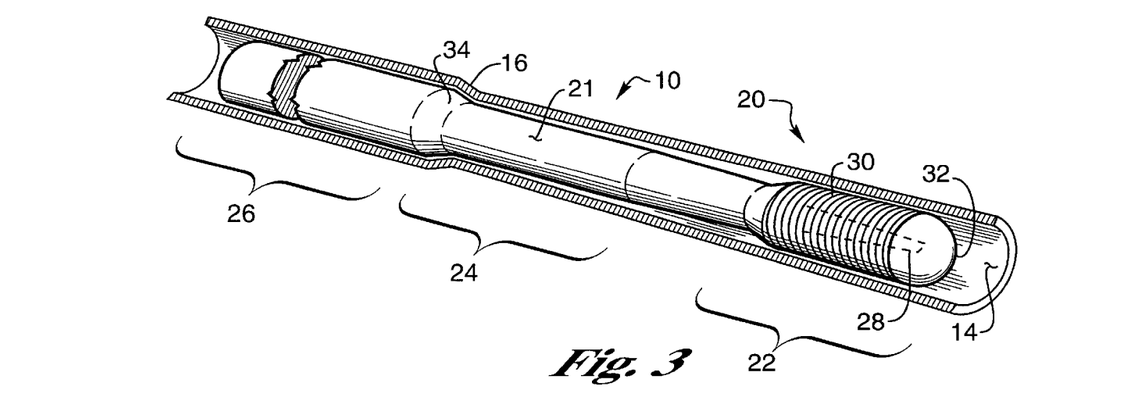
FIG. 3 is a cross-sectional view of a cardiac lead with a guidewire of FIG. 2 positioned within the lumen of the lead.

FIG. 3 shows the guidewire 20 of FIG. 2 positioned within a lumen 14 of the coronary lead 10. The lumen 14 preferably has a transition 16 which corresponds to the shoulder 34 of the guidewire 20. When the shoulder 34 engages the transition 16, advancement forces applied to the guidewire 20 during insertion of the guidewire 20 are transferred to the lead 10 through the shoulder 34 and transition 16 which is a reduction in lumen diameter. Similarly when the guide catheter 8, FIG. 1, is extracted from the lead 20, transition 16 is held in place by shoulder 34 the guidewire 20.

Figure 4:
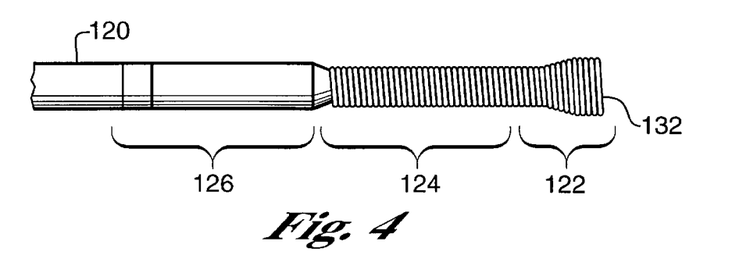
FIG. 4 is a plan view of an embodiment of a removal wire made in accordance with the present invention.
Figure 5:
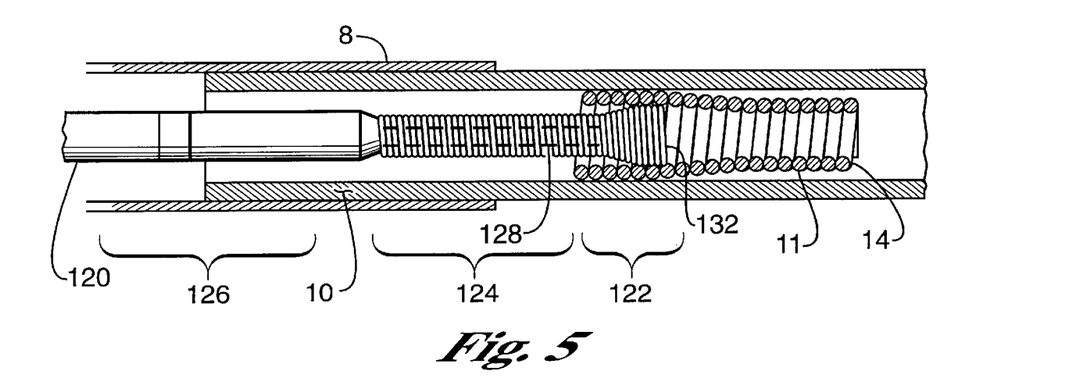
FIG. 5 is a cross-sectional view of a cardiac lead surrounded by a guide catheter and with a removal wire of the type shown in FIG. 4 positioned within the lumen of the lead.

FIGS. 4 and 5 show another embodiment of a guidewire 120. This type of guidewire 120 is referred to herein as a removal wire or removal wire. It is ideally suited for use during removal of a guide catheter 8 to prevent lead displacement. After a guidewire is used to insert the lead, the guidewire is first withdrawn and replaced by a removal wire 120 that is inserted to retain the lead 10 in place during extraction of the surrounding guide catheter 8. Again, the removal wire 120 of this embodiment may comprise three zones—a distal zone 122, an intermediate zone 124, and a proximal zone 126. The removal wire 120 shown in FIGS. 4 and 5 is dimensioned somewhat in a fashion similar to the guidewire shown in FIGS. 2 and 3. The primary difference between the removal wire shown in FIGS. 4 and 5 and the guidewire shown in FIGS. 2 and 3 is that the distal tip 132 in FIGS. 4 and 5 are not attached to the core 128 by a solder joint. Also, the distal tip 132 of this embodiment is not intended to exit the distal end of the lead 10, thus it is not shapeable or steerable in the vasculature nor is an atraumatic spherical tip required. Finishing wire 120 may be used to lock into the lead 10 and transmit force to the lead tip, but is only used in conjunction with the lead 10 during removal of the guide catheter 8. The spiral wound wire in the intermediate zone 124 may be secured to the proximal zone 126 by a solder joint or by crimping. The direction of the winding 124 will preferably be opposite that of any winding 11 of the elongated conductor of lead 10 itself. This allows for better tracking through the central lumen 14 of the lead 10. The distal zone 122 is a continuation of the spiral winding of the intermediate zone 124. However, the diameter of the winding increases to form the distal zone 122. The distal tip 132 of the coil which forms the intermediate end distal zones is cut square and not attached to a core wire or the like. Thus, as the guide catheter 8 is withdrawn, the square cut of tip 132 seats in the taper of the coil 11 of the lead 10 preventing the lead from withdrawing as the guide catheter 8 is pulled free. Furthermore, as the removal wire 20 is pulled free from the lead 10, the square, unattached coil tip 132 slightly distends and easily frees itself from the tapered coil section 11 of the lead 10. This feature allows for easy, predictable removal of the removal wire 120 from the lead 10, thus preventing loss of purchase of the lead upon its withdrawal.

Figure 7:
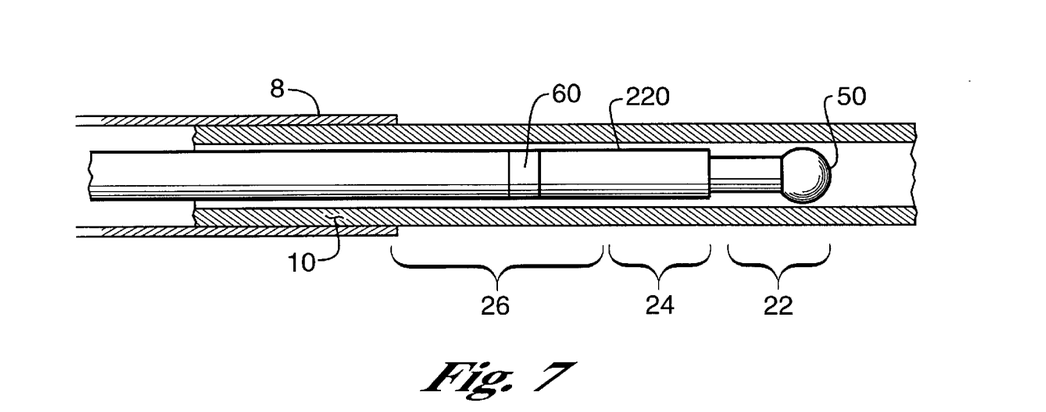
FIG. 7 is a cross-section of a guide catheter, lead and removal wire with a spherical tip and a temporary locking mechanism in the proximal zone.
Figure 8:
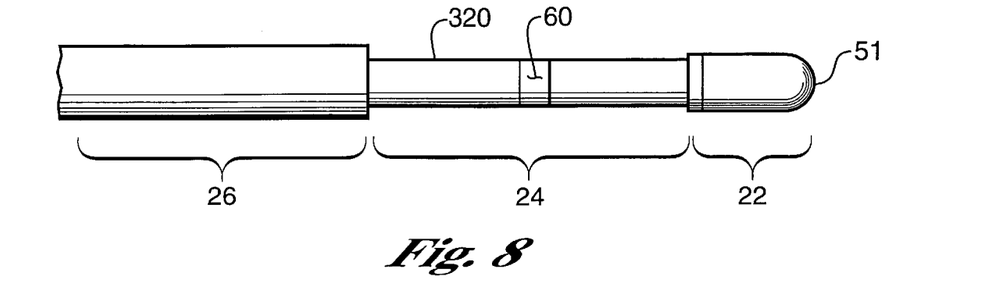
FIG. 8 is a fragmentary side view of a removal wire with a bullet tip and a temporary locking mechanism in the intermediate zone.
Figure 9:
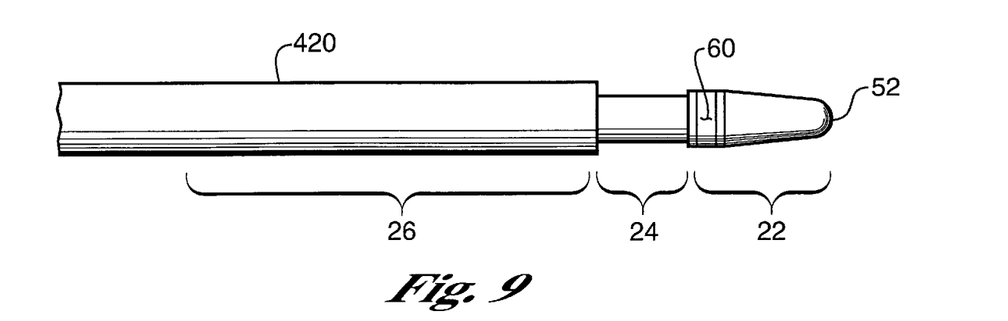
FIG. 9 is a fragmentary side view of a removal wire with a tapered tip and a temporary locking mechanism in the distal zone.

In other embodiments, a removal wire 220, 320 and 420, as shown in FIGS. 7, 8, and 9, respectively, may be used to extract the guide catheter 8 while leaving the lead 10 and its electrodes in place. As shown in FIG. 7, the removal wire 220 is inserted into the lead 10 and extends some distance past the distal end of the guide catheter 8, but short of the end of the lead 10. Although FIG. 7 is shown with the catheter guide 8, lead 10 and removal wire 220 in a concentric, collinear relation, when, inside of the heart, they really have a curved tortuous path. The catheter guide 8, lead 10 and removal wire 220 will be in frictional contact with each other over a curved path. The lead 10 will be in frictional contact with the guide catheter 8 making it difficult to withdraw the guide catheter 8 without applying a force to the lead 10 that tends to withdraw the lead. It is desired to leave the lead in its originally placed position to maintain the optimal placement of the electrodes. The removal wire 220 is used to maintain the lead 10 in place while withdrawing the guide catheter 8. Since the removal wire 220 extends beyond the length of the guiding catheter 8 the total frictional contact area between the removal wire 220 and the lead 10 will be greater than the frictional contact area between the guide catheter 8 and the lead 10, thus the lead 10 will tend to stay in place as the guide catheter 8 is withdrawn, particularly if the removal wire 220 extends substantially past the end of the guide catheter 8 and is maintained stationary. Following removal of the guide catheter, the removal wire can be removed by extracting it from the lumen 14 of the lead 10 by simply pulling it out while holding the proximal end of the lead to prevent it from being dislodged from the position it had been placed in.

As shown in FIG. 7 the removal wire 220 has a spherical tip 50 for ease of inserting and withdrawing the removal wire 220 over the length of lead 10. FIG. 8 shows a removal wire 320 having a bullet shaped tip 51 for ease of inserting and withdrawing the removal wire 320 in the lead 10. FIG. 9 shows another embodiment of the removal wire 420 with a tapered tip 52. The tips 50, 51 and 52 on the removal wires 220, 320 and 420 should be atraumatic tips to avoid punctures of the leads 10 and the veins in case the removal wire is allowed to exit the distal end of lead 10.

In other embodiments the spherical tip 50, the bullet tip 51 and the tapered tip 52 may be made to frictionally contact lead 10 to help hold the lead in place.

In the embodiments of FIGS. 7, 8 and 9 the removal wires 220, 320, and 420 may have additional means 60 for temporarily locking to the lead 10 at the distal end of the lead 10 such that the guide catheter 8 can be removed without the lead 10 being dislodged. Any number of means for temporarily locking the lead 10 at the distal end of the removal wire may be employed. For example, in U.S. Pat. No. 5,011,482 to Goode et al., FIGS. 10 to 19 disclose expandable balloons, and radially expanding projections, such as deformable strips, radially expanding barbs, expanding sleeves, and off center (eccentric) cylinders on the removal wire for temporarily locking the removal wire onto the lead and holding the lead in place while a guide catheter is removed. In Goode et al U.S. Pat. No. 5,013,310 a wire is radially unwound for engaging the lead and locking the lead in place. In Pearson et al. U.S. Pat. No. 5,769,858 the distal end of the removal wire is bent into a J-shape hook at the distal end for engaging the lead and holding it in place while the guide catheter is removed. These patents show some means, but not the only means, for temporarily locking the distal end of the removal wire to the lead. U.S. Pat. Nos. 5,769,858, 5,013,310 and 5,011,482 are hereby incorporated herein by reference.

Alternatively, the removal wires 20, 120, 220, 320, and 420 in the several embodiments may have a means of temporarily locking to the lead 10 at the proximal end of the lead, as at locking connection 80 shown in FIG. 1 abutting the proximal end of the terminal pin 70, such that the lead 10 will be held in place while the guide catheter 8 is removed by slipping it back over the locking connection 80. In another embodiment shown in FIG. 1A, the locking connection 80' comprises a suture 81 where the suture affixed to the removal wire 20 is made to abut the proximal end of the leads terminal pin 70 to hold the lead in place as the guide catheter 8 is removed. In another embodiment, the locking connection 80 can be achieved by slipping a short length of hypo tubing over the removal wire and bonding or welding the two together, such that he distal end of the hypo tube 80' creates a shoulder that abuts the free end of terminal pin 70. See FIG. 1B. In still other embodiments the terminal pin 70 may have a collet or other temporary locking device for engaging and holding the lead 10 in place on the removal wire. The locking element must be sufficiently small in size to allow the guide catheter to strip over it. In some embodiments, both the distal temporary locking mechanism 60 and the proximal temporary locking mechanism 80 can be used simultaneously.

Although the removal wires 20, 120, 220, 320 and 420 shown in the various figures may be of the three-zone design, they need not necessarily have a distal zone 22 which is designed to be very flexible since the removal wire need not exit the distal end of the lead. Similarly the removal wires may not need an intermediate zone 24 since the flexibility inside of the lead is not as much of an issue as when the guidewire and the lead were in the vein without a guide catheter. However, the removal wires have to be flexible enough to snake their way through the lead 10 without damaging the lead or exiting the lead and damaging the vein in which the lead is located. The removal wire may have one continuous zone for this purpose. The distal tips may be of the spherical, bullet or tapered designs. Such removal wires may have just a single zone, or both a proximal zone and a flexible distal zone, or a proximal zone, an intermediate zone, and a flexible distal zone.

For removal wires 20, 120, 220, 320, 420 with a distal zone 22, a intermediate zone 24 and a proximal zone 26 a temporary locking means 60 is preferably used in the proximal zone 26 for greatest locking stability and stiffness. However the temporary locking means 60 may be in the distal zone 22 or the intermediate zone 24.

Figure 10:
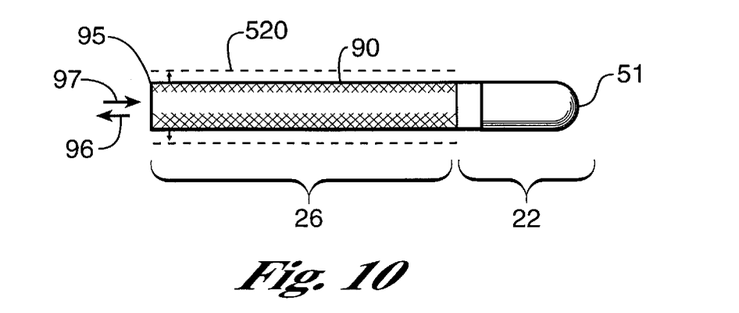
FIG. 10 is a partial side view of a removal wire having a proximal zone and a distal zone with a bullet tip and an expandable element as a temporary locking mechanism on a large portion of the length of the proximal zone of the removal wire.

In another embodiment shown in FIG. 10, the entire length or a predetermined portion of the removal wire 20 within the lead can be expanded, such as with a braided element 90, to temporarily lock the removal wire 20 securely to the lead. The element 90 acts like so-called "Chinese handcuffs". It expands by contracting the braided wire mesh material along its length by moving the edge 95 thereof in direction 97. The radius of the braided element thereby increases to provide a large surface contact area and, thus, firm grip on the lead 10. The braided element 90 is radially retracted by pulling the braided element at the edge of the element 95 in direction 96. In this manner the removal wire is unlocked from the lead. A braided element 90 may be of a shorter length and be used as the temporary locking means 60 in the embodiments of FIGS. 7, 8, and 9.

In all of the embodiments, a hydrophilic coating can be applied to create a surface 21 (FIG. 3) on the guidewire 20 that is highly lubricious. Alternatively, all surfaces of guidewire 20 can be coated with a hydrophilic coating, of polytetrafluoroethylene (PTFE), or some other dry lubricious material, i.e. silicone film. This serves to reduce friction between the guidewire 20 and lead lumen 14 of the lead thereby reducing the risk that the lead 10 will be dislodged from its proper position as the guidewire 20 is extracted.

What is claimed is:

1. A method for installing an intravenous pacing lead within a patient, comprising:
    advancing a guide catheter through a vasculature until a distal end of the guide catheter is located in the coronary sinus of the heart;
    advancing the pacing lead over at least a portion of a guidewire to position the pacing lead adjacent tissue to be stimulated, wherein at least a portion of the pacing lead is maintained within a lumen of the guide catheter and at least a portion of the guidewire is located within a lumen of the pacing lead;
    removing the guidewire from the pacing lead lumen;
    inserting a removal wire into the pacing lead lumen after removing the guidewire to secure the lead; and
    removing the guide catheter from said portion of the pacing lead maintained within the lumen of the guide catheter while the removal wire is securing the lead.

2. The method of claim 1, wherein the step of inserting the removal wire into the pacing lead lumen includes inserting the removal wire until it abuts against a reduced diameter section of the pacing lead lumen.

3. The method of claim 2, wherein the reduced diameter section includes a taper.

4. The method of claim 3, wherein the reduced diameter section is formed by a coiled member of the pacing lead.

5. The method of claim 1, further including the step of removing the removal wire from the pacing lead lumen.

6. The method of claim 1, further comprising temporally securing the removal wire to the pacing lead prior to removing the guide catheter.

7. The method of claim 6, wherein the step of temporally securing the removal wire to the pacing lead includes abutting a proximal portion of the removal wire against a proximal end of the pacing lead.

8. The method of claim 6, further comprising unsecuring the removal wire from the pacing lead and removing the removal wire from the pacing lead lumen.

9. The method of claim 1, wherein the step of inserting the removal wire into the pacing lead lumen includes locating a distal end portion of the removal wire distal of the distal end of the guide catheter so that the removal wire has a greater frictional contact area with the pacing lead than the guide catheter has with the pacing lead.

10. The method of claim 1, wherein the removal wire has a square distal tip.

11. The method of claim 1, wherein the removal wire has a rounded distal tip.

12. A method for installing an intravenous pacing lead within a patient, comprising:
    advancing a guide catheter through a vasculature until a distal end of the catheter is located in the coronary sinus of the heart;
    advancing the pacing lead to position the pacing lead adjacent tissue to be stimulated, wherein at least a portion of the pacing lead is maintained within a lumen of the guide catheter and at least a portion of a guidewire is located within a lumen of the pacing lead;
    removing the guidewire from the pacing lead lumen;
    inserting a removal wire into the pacing lead lumen after removing the guidewire to secure the lead; and
    removing the guide catheter from said portion of the pacing lead maintained within the lumen of the guide catheter while the removal wire is securing the lead.

13. The method of claim 12, wherein the step of inserting the removal wire into the pacing lead lumen includes inserting the removal wire until it abuts against a reduced diameter section of the pacing lead lumen.

14. The method of claim 13, wherein the reduced diameter section includes a taper.

15. The method of claim 14, wherein the reduced diameter section is formed by a coiled member of the pacing lead.

16. The method of claim 12, further including the step of removing the removal wire from the pacing lead lumen.

17. The method of claim 12, further comprising temporally securing the removal wire to the pacing lead prior to removing the guide catheter.

18. The method of claim 17, wherein the step of temporally securing the removal wire to the pacing lead includes abutting a proximal portion of the removal wire against a proximal end of the pacing lead.

19. The method of claim 17, further comprising unsecuring the removal wire from the pacing lead and removing the removal wire from the pacing lead lumen.

20. The method of claim 13, wherein the step of inserting the removal wire into the pacing lead lumen includes locating a distal end portion of the removal wire distal of the distal end of the guide catheter so that the removal wire has a greater frictional contact area with the pacing lead than the guide catheter has with the pacing lead.

21. The method of claim 13, wherein the removal wire has a square distal tip.

22. The method of claim 13, wherein the removal wire has a rounded distal tip.

23. An intravenous lead insertion assembly, comprising
a catheter having a proximal end and a distal end;
an intravenous lead at least partially located within the catheter and having at least one electrode and a lumen extending from a proximal end of the lead to a distal end of the lead, the lumen having a first opening through the proximal end of the lead and a second opening through the distal end of the lead;
a guidewire for facilitating advancement of the intravenous lead into the coronary sinus, said guidewire sized to extend through the first and second openings in said lumen and past the distal end of the lead during implantation of the lead, and being removable from the lead after placement of the lead in the coronary sinus; and
a removal wire sized to extend through the first opening and into the lumen of the intravenous lead, the removal wire having a distal end portion including a lead contacting portion for contacting the lead to facilitate securing the lead during a removal of the catheter from around the lead.

24. The intravenous lead insertion assembly according to claim 23, wherein the lumen of the intravenous lead is of a size to separately receive the guidewire and the removal wire, but is not of a size to receive the guidewire and the removal wire simultaneously.

25. The intravenous lead insertion assembly according to claim 23, wherein the distal end of the intravenous lead extends distal of the distal end of the catheter prior to removal of the catheter.

26. The intravenous lead insertion assembly according to claim 23, wherein the contacting portion of the removal wire abuts a portion of the intravenous lead.

27. The intravenous lead insertion assembly according to claim 23, wherein the contacting portion of the removal wire contacts the lumen of intravenous lead.

28. The intravenous lead insertion assembly according to claim 23, wherein the contacting portion of the removal wire includes a transition portion located between a larger diameter section of the removal wire and a smaller diameter section of the removal wire.

29. The intravenous lead insertion assembly according to claim 28, wherein the lumen of the intravenous lead includes a first diameter portion and a second diameter portion, the second diameter portion being smaller than the first and located distal of the first diameter.

30. The intravenous lead insertion assembly according to claim 29, wherein the lumen of the intravenous lead includes a tapered portion between the first and second diameter portions.

31. The intravenous lead insertion assembly according to claim 23, wherein the contacting portion of the removal wire provides a frictional engagement with the lumen of the intravenous lead.

32. The intravenous lead insertion assembly according to claim 23, wherein the removal wire includes a spherical distal tip.

33. The intravenous lead insertion assembly according to claim 23, wherein the removal wire includes a bullet shaped distal tip.

34. The intravenous lead insertion assembly according to claim 23, wherein the removal wire includes a tapering distal tip.

35. The intravenous lead insertion assembly according to claim 23, wherein the removal wire includes a coiled member forming a squared distal tip.

36. The intravenous lead insertion assembly according to claim 23, wherein the lumen of the intravenous lead is formed by a helical coil and the contacting portion engages the helical coil of the lead.

37. The intravenous lead insertion assembly according to claim 23, wherein the lumen of the intravenous lead is formed by a helical coil.

38. An intravenous lead insertion assembly, comprising
a catheter having a proximal end and a distal end;
an intravenous cardiac pacing lead at least partially located within the catheter and having at least one pacing electrode and a lumen extending from a proximal end of the lead to a distal end of the lead, the lumen having a first opening through the proximal end of the lead and a second opening through the distal end of the lead;
a guidewire for facilitating advancement of the intravenous lead into the coronary sinus, said guidewire sized to extend through the first and second openings in said lumen and past the distal end of the lead during implantation of the lead, and being removable from the lead after placement of the lead in the coronary sinus; and
a removal wire sized to extend through the first opening and into the lumen of the intravenous lead, the removal wire having a distal end portion including a lead contacting portion for contacting the lead to facilitate securing the lead during a removal of the catheter from around the lead.

39. The intravenous lead insertion assembly according to claim 38, wherein the lumen of the intravenous lead is of a size to separately receive the guidewire and the removal wire, but is not of a size to receive the guidewire and the removal wire simultaneously.

40. The intravenous lead insertion assembly according to claim 38, wherein the contacting portion of the removal wire abuts the intravenous lead.

41. The intravenous lead insertion assembly according to claim 38, wherein the contacting portion of the removal wire includes a transition portion located between a larger diameter section of the removal wire and a smaller diameter section of the removal wire.

42. The intravenous lead insertion assembly according to claim 38, wherein the removal wire includes a spherical distal tip.

43. The intravenous lead insertion assembly according to claim 38, wherein the lumen of the intravenous lead is formed by a helical coil.

44. An intravenous lead insertion assembly, comprising a catheter having a proximal end and a distal end;

an intravenous cardiac lead at least partially located within the catheter and having at least one defibrillation electrode and a lumen extending from a proximal end of the lead to a distal end of the lead, the lumen having a first opening through the proximal end of the lead and a second opening through the distal end of the lead;

a guidewire for facilitating advancement of the intravenous lead into the coronary sinus, said guidewire sized to extend through the first and second openings in said lumen and past the distal end of the lead during implantation of the lead, and being removable from the lead after placement of the lead in the coronary sinus; and a removal wire sized to extend through the first opening and into the lumen of the intravenous lead, the removal wire having a distal end portion including a lead contacting portion for contacting the lead to facilitate securing the lead during a removal of the catheter from around the lead.

45. The intravenous lead insertion assembly according to claim 44, wherein the lumen of the intravenous lead is of a size to separately receive the guidewire and the removal wire, but is not of a size to receive the guidewire and the removal wire simultaneously.

46. The intravenous lead insertion assembly according to claim 44, wherein the contacting portion of the removal wire abuts a portion of the intravenous lead.

47. The intravenous lead insertion assembly according to claim 44, wherein the contacting portion of the removal wire includes a transition portion located between a larger diameter section of the removal wire and a smaller diameter section of the removal wire.

48. The intravenous lead insertion assembly according to claim 44, wherein the removal wire includes a spherical distal tip.

49. The intravenous lead insertion assembly according to claim 44, wherein the lumen of the lead is formed by a helical coil.

* * * * *

UNITED STATES PATENT AND TRADEMARK OFFICE
CERTIFICATE OF CORRECTION

PATENT NO. : 6,671,560 B2  
DATED : December 30, 2003  
INVENTOR(S) : Randy W. Westlund et al.

It is certified that error appears in the above-identified patent and that said Letters Patent is hereby corrected as shown below:

<u>Column 9,</u>  
Lines 12, 18 and 20, replace "claim 13" with -- claim 12 --; and  
Line 66, replace "first and" with -- first diameter and --.

Signed and Sealed this

Ninth Day of March, 2004

JON W. DUDAS  
*Acting Director of the United States Patent and Trademark Office*